United States Patent [19]

Malhotra

[11] 4,132,784
[45] Jan. 2, 1979

[54] (SUBSTITUTED PYRIDYL)PHENOXY PHOSPHORUS COMPOUNDS AND THEIR USE AS INSECTICIDES

[75] Inventor: Sudarshan K. Malhotra, Contra Costa, Calif.

[73] Assignee: The Dow Chemical Company, Midland, Mich.

[21] Appl. No.: 848,051

[22] Filed: Nov. 3, 1977

Related U.S. Application Data

[60] Division of Ser. No. 746,977, Dec. 2, 1976, Pat. No. 4,080,443, which is a continuation-in-part of Ser. No. 646,808, Jan. 6, 1976, abandoned.

[51] Int. Cl.$^2$ .................. A01N 9/22; C07D 213/02; C07D 213/57
[52] U.S. Cl. ........................ 424/200; 546/24; 546/25; 546/288; 546/296; 546/297; 546/294; 546/295; 546/301; 546/302
[58] Field of Search .............. 260/294.8 K, 297 P, 260/294.9; 424/200

[56] References Cited

U.S. PATENT DOCUMENTS 3,968,222  7/1976  Drabek et al. .................. 424/200

*Primary Examiner*—Alan L. Rotman
*Attorney, Agent, or Firm*—S. Preston Jones; C. Kenneth Bjork

[57] ABSTRACT

Compounds are prepared which correspond to the formula

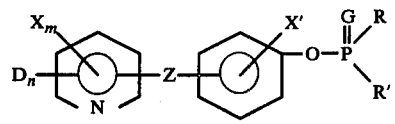

wherein each X independently represents chloro, fluoro or bromo; X' represents hydrogen, methyl, chloro, fluoro or bromo; G represents oxygen or sulfur; Z represents oxygen, sulfur, sulfinyl or sulfonyl, with the proviso that Z is attached to the pyridine ring in only the 2 or 4 ring position; D represents cyano, nitro, trifluoromethyl, loweralkyl, loweralkoxy, loweralkylsulfonyl, loweralkylthio, or the radical

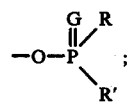

R represents loweralkoxy, loweralkylamino or diloweralkylamino; R' represents R or phenyl; m represents an integer of from 0 to 4; n represents 0 or 1 and the sum of m + n represents an integer of from 0 to 4.

The compounds have been found to be effective insect control agents.

3 Claims, No Drawings

(SUBSTITUTED PYRIDYL)PHENOXY PHOSPHORUS COMPOUNDS AND THEIR USE AS INSECTICIDES

CROSS-REFERENCE TO RELATED APPLICATION

This application is a divisional of application Ser. No. 746,977 filed Dec. 2, 1976, now U.S. Pat. No. 4,080,443, which in turn is a continuation-in-part of application Ser. No. 646,808, filed Jan. 6, 1976, now abandoned.

SUMMARY OF THE INVENTION

The present invention is directed to novel compounds corresponding to the formula

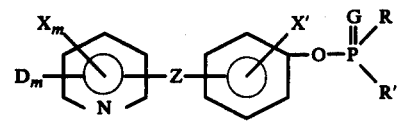

In this and succeeding formulae, each X independently represents chloro, fluoro or bromo; X' represents hydrogen, methyl, chloro, fluoro or bromo; G represents oxygen or sulfur; Z represents oxygen, sulfur, sulfinyl or sulfonyl, with the proviso that Z is attached to the pyridine ring in only the 2 or 4 ring position; D represents cyano, nitro, trifluoromethyl, loweralkyl of 1 to 2 carbon atoms, loweralkoxy of 1 to 2 carbon atoms, loweralkylsulfonyl of 1 to 2 carbon atoms, of 1 to 2 carbon atoms loweralkylthio of 1 to 4 carbon atoms or the radical

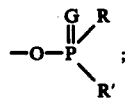

R represents loweralkylthio, loweralkoxy, loweralkylamino of 1 to 2 carbon atoms or diloweralkylamino of 1 to 2 carbon atoms; R' represents R or phenyl; m represents an integer of from 0 to 4; n represents 0 or 1 and the sum of m + n represents an integer of from 0 to 4.

The organophosphorus compounds of the present invention are crystalline solids or oils which are of low solubility in water and soluble in common organic solvents. The compounds have been found to be active insect control agents for the kill and control of many common household, industrial and agricultural insects. Such insects include houseflies, copper bottle fly, mosquito larva and adults, two spotted spider mite, cabbage looper, cucumber beetle, codling moth, bollworm and cockroach. The compounds have low vapor-pressure which enhances their persistence as insecticides and in addition, they exhibit low mammalian toxicity.

The new compounds of the present invention can be prepared by reacting an appropriate pyridyl(oxy-, thio-, sulfinyl- or sulfonyl-) phenol with an appropriate phosphorochloridate in the presence of a solvent and a base such as, for example, an alkali metal hydroxide or carbonate.

The following reaction scheme A illustrates the preparation of the novel compounds of the present invention.

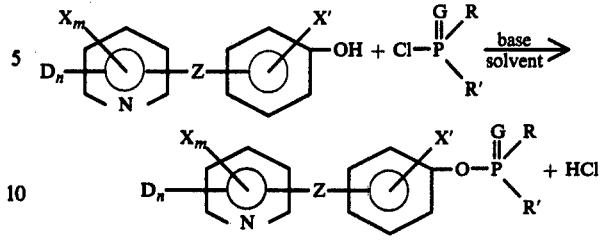

wherein Z, G, R, R', D, X, X' m and n are as set forth hereinabove.

The above reaction is conveniently carried out by contacting the reactants together in a solvent such as, for example, monoglyme, hexamethylphosphoramide, acetonitrile, dimethylformamide or mixtures thereof and in the presence of a base such as, for example, sodium or potassium hydroxide or sodium or potassium carbonate. The reaction takes place smoothly at atmospheric pressure and temperatures between about 0° and the reflux temperature of the reaction mixture. The reaction is conveniently carried out at room temperature.

In carrying out the reaction, the reactants are contacted together in at least equimolar proportions of the phenol reactant to the phosphorus reactant. The base is usually employed in an amount of from about 1.0 to about 1.5 moles per mole of the phenol reactant. The reactants are maintained under the aforedescribed conditions until the reaction is substantially complete, usually from about 2 to about 72 hours.

The reaction mixture is diluted with water and extracted with a solvent such as, for example, methylene chloride, hexane, benzene, chloroform or carbon tetrachloride. The extract is washed with a dilute basic solution and/or water and dried and the solvent removed by evaporation under reduced pressure leaving the desired product as a residue.

The compounds of the present invention wherein D is the radical

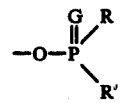

can be prepared by reacting one molecular equivalent of an appropriate hydroxy substituted pyridyl(oxy-, thio-, sulfinyl- or sulfonyl)phenol with two molecular equivalents of an appropriate phosphorochloridate in the presence of a solvent and a base such as those set forth hereinabove.

The following reaction scheme illustrates the preparation of the above novel compounds of the present invention.

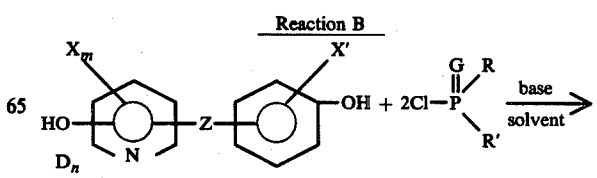

-continued
Reaction B

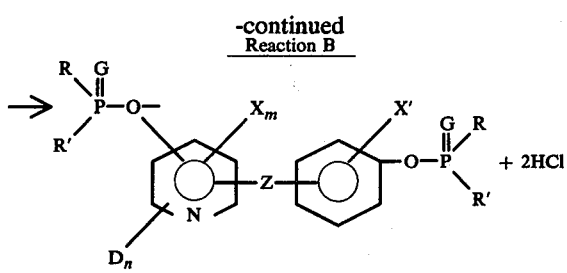

The above reaction can be carried out in the same manner as set forth hereinabove for Reaction A and the teachings thereto are incorporated here by reference thereto.

DESCRIPTION OF SOME PREFERRED EMBODIMENTS

The following examples illustrate the present invention and the manner by which it can be practiced, but as such, should not be construed as limitations upon the overall scope of the same.

EXAMPLE I 0,0-Diethyl-0-[4-((6-chloro-2-pyridyl)oxy)-phenyl]-phosphorothioate

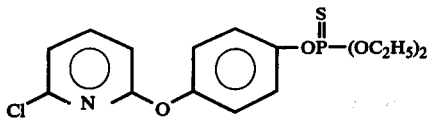

A mixture consisting of one (1) gram (0.005 mole) of 4-((6-chloro-2-pyridyl)oxy)phenol, 0.75 gram of anhydrous potassium hydroxide and one (1) gram (0.006 mole) of 0,0-diethyl chlorothiophosphate in 50 milliliters of a 1:1 mixture of monoglyme and hexamethylphosphoramide was stirred at room temperature for 2 hours. The mixture was diluted with water and exhaustively extracted with hexane. The hexane extract was washed with water and dried over anhydrous magnesium sulfate. The hexane was removed by evaporation under reduced pressure leaving 1.45 grams (81 percent of theoretical) of 0,0-diethyl-0-[4-((6-chloro-2-pyridyl)oxy)phenyl]phosphorothioate, an oily material having a refractive index of n $^{25}$/d = 1.5350 (compound 1). The structure of the product was confirmed by Nuclear Magnetic Resonance (NMR) and thin layer chromatography (TLC).

EXAMPLE II 0,0-Diethyl-0-[4-((6-fluoro-2-pyridyl)thio)phenyl]-phosphorothioate

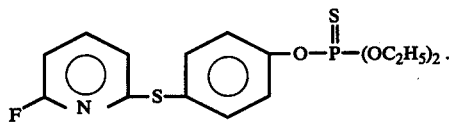

A mixture of 10 grams (0.05 mole) of 4-((6-fluoro-2-pyridyl)thio)phenol, 8.6 grams (0.05 mole) of 0,0-diethyl chlorothiophosphate and 3 grams of anhydrous potassium hydroxide in 150 milliliters of a 1:1 mixture of monoglyme and hexamethylphosphoramide was stirred overnight (about 16 hours) at room temperature. The resulting mixture was diluted with water and thereafter thoroughly extracted with hexane. The hexane extract was washed with water, dried over anhydrous magnesium sulfate and the hexane was removed by evaporation under reduced pressure leaving the 0,0-diethyl-0-[4-((6-fluoro-2-pyridyl)thio)phenyl]phosphorothioate product as an oil (compound 2). The product was obtained in a yield of 10 grams (53 percent of theoretical) and had a refractive index of n $^{25}$/d = 1.5555 and the structure of the product was confirmed by NMR and TLC.

EXAMPLE III 0,0-Diethyl 0-[4-((6-methoxy-2-pyridyl)thio)-phenyl]phosphorothioate

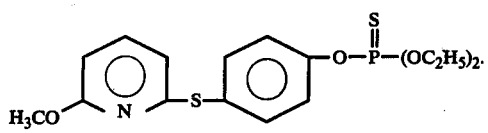

A mixture consisting of 35 grams (0.15 mole) of 4-((6-methoxy-2-pyridyl)thio)phenol, 28.3 grams (0.145 mole) of diethyl chlorothiophosphate and 24.8 grams (0.18 mole) of anhydrous potassium carbonate in 500 milliliters of acetonitrile was heated under reflux overnight (~ 16 hours). Thereafter, most of the acetonitrile was removed by evaporation under reduced pressure and the resulting residue was diluted with water and extracted with methylene chloride. The methylene chloride extract was first washed with a dilute sodium hydroxide solution followed by washing with water. The extract was thereafter dried and the methylene chloride removed by evaporation under reduced pressure leaving the 0,0-diethyl 0-[4-((6-methoxy-2-pyridyl)-thio)phenyl]phosphorothioate product as a yellow oil. The product was recovered in a yield of 50.5 grams (87 percent of theoretical) and had a refractive index of n$^{25}$/d = 1.5326 (compound 3). The structure of the product was confirmed by NMR and TLC.

EXAMPLE IV 0,0-Diethyl 0-[6-(4-(((-diethoxyphosphinothioyl)oxy)phenyl)thio)-2-pyridyl]phosphorothioate

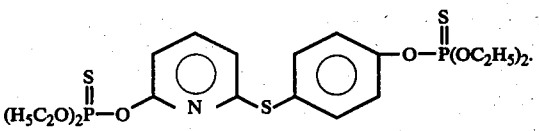

A mixture consisting of 2.2 grams (0.01 mole) of 4-((6-hydroxy-2-pyridyl)thio)phenol, 3.76 grams (0.02 mole) of diethyl chlorothiophosphate and 3.45 grams (0.025 mole) of anhydrous potassium carbonate was stirred in 50 milliliters of acetonitrile and heated at reflux overnight (~ 16 hours). Thereafter, most of the acetonitrile was removed by evaporation under reduced pressure. The residue was diluted with water and extracted thoroughly with methylene chloride. The methylene chloride extract was washed with water, dried and the solvent removed by evaporation under reduced pressure. The 0,0-diethyl 0-[6-(4-(((-diethoxyphosphinothionyl)oxy)phenyl)thio)-2-pyridyl]phosphorothioate product, a yellow oil, was recovered in a yield of 4.1 grams (78 percent of theoretical and had a refractive index of n $^{25}$/d = 1.5651 (compound 4). The structure of the compound was confirmed by NMR and TLC.

By following the preparative procedures outlined in the above Examples, the following compounds as set forth in Table I are prepared.

TABLE I

Structure: pyridine ring (with $X_m$, $D_N$) — Z — phenyl ring (with X') — O — P(=G)(R)(R')

| Compound No. | D | X | X' | Z | O | G | R | R' | Method of Preparation | Physical[a] Properties |
|---|---|---|---|---|---|---|---|---|---|---|
| 5 | 6-CF$_3$ | — | — | 2-O | 4- | S | —OC$_2$H$_5$ | —OC$_2$H$_5$ | A | n 25/d = 1.5002 |
| 6 | — | 6-Br | — | 2-O | 4- | S | —OC$_2$H$_5$ | —OC$_2$H$_5$ | A | n 25/d = 1.5460 |
| 7 | — | 6-Br | 4-Br | 2-O | 2- | S | —OCH$_3$ | —OCH$_3$ | A | M.W. = 468.00 |
| 8 | — | 3,5,6-Cl | — | 2-O | 4- | S | —OC$_2$H$_5$ | —OC$_2$H$_5$ | A | n 25/d = 1.5712 |
| 9 | — | 6-Cl | — | 2-S | 4- | S | —OC$_2$H$_5$ | —OC$_2$H$_5$ | A | n 25/d = 1.5821 |
| 10 | 6-SCH$_3$ | 3,5-Cl | — | 2-O | 4- | S | —OC$_2$H$_5$ | —OC$_2$H$_5$ | A | M.P. 56° – 60° C |
| 11 | — | 3,5,6-Cl | — | 2-S | 4- | S | —OC$_2$H$_5$ | —OC$_2$H$_5$ | A | M.W. 458.5 |
| 12 | — | 6-F;3,5-Cl | 3-Cl | 2-S | 4- | S | —OC$_2$H$_5$ | —OC$_2$H$_5$ | A | M.W. = 476.62 |
| 13 | 6-CF$_3$ | — | — | 2-S | 4- | S | —OC$_2$H$_5$ | —OC$_2$H$_5$ | A | n 25/d = 1.5364 |
| 14 | — | 6-F;3,5-Cl | — | 2-S | 4- | S | —OC$_2$H$_5$ | —OC$_2$H$_5$ | A | M.W. 442.18 |
| 15 | — | 2,3,5-Cl | — | 4-S | 4- | S | —OC$_2$H$_5$ | —OC$_2$H$_5$ | A | n 25/d = 1.5768 |
| 16 | 6-CN | — | — | 2-S | 4- | S | —OC$_2$H$_5$ | —OC$_2$H$_5$ | A | M.W. = 381.28 |
| 17 | — | 6-F;3,5-Cl | 3-CH$_3$ | 2-S | 4- | S | —OCH$_3$ | —OCH$_3$ | A | M.W. 428.01 |
| 18 | — | 3,6-Cl | — | 2-S | 4- | S | —OC$_2$H$_5$ | —OC$_2$H$_5$ | A | M.P. = 42° –;0 45° C |
| 19 | — | 2,6-Cl | — | 4-S | 4- | S | —OC$_2$H$_5$ | —OC$_2$H$_5$ | A | M.W. = 424.18 |
| 20 | — | 3,5-Cl | — | 2-S | 4- | S | —OC$_2$H$_5$ | —OC$_2$H$_5$ | A | n 25/d = 1.5936 |
| 21 | — | 3-Cl | — | 2-S | 4- | S | —OC$_2$H$_5$ | —OC$_2$H$_5$ | A | M.P. = 54° – 57° C |
| 22 | 5-NO$_2$ | — | — | 2-S | 4- | S | —OC$_2$H$_5$ | —OC$_2$H$_5$ | A | M.P. = 42° – 45° C |
| 23 | — | 6-Cl | 3-Cl | 2-S | 4- | S | —OC$_2$H$_5$ | —OC$_2$H$_5$ | A | n 25/d = 1.5955 |
| 24 | — | 6-F | 3-Cl | 2-S | 4- | S | —OC$_2$H$_5$ | —OC$_2$H$_5$ | A | n 25/d = 1.5777 |
| 25 | — | 3-Cl | 3-Cl | 2-S | 4- | S | —OC$_2$H$_5$ | —OC$_2$H$_5$ | A | n 25/d = 1.5995 |
| 26 | — | 6-Br | — | 2-S | 4- | S | —OC$_2$H$_5$ | —OC$_2$H$_5$ | A | n 25/d = 1.6031 |
| 27 | 6-CH$_3$ | 3,5-Cl | 3-Cl | 2-S | 4- | S | —OCH$_3$ | —OCH$_3$ | A | M.W. = 411.55 |
| 28 | 6-C$_2$H$_5$ | — | — | 2-S | 3- | S | —OCH$_3$ | —OCH$_3$ | A | M.W. = 350.40 |
| 29 | — | 6-Br | 3-Cl | 2-S | 4- | S | —OC$_2$H$_5$ | —OC$_2$H$_5$ | A | M.W. = 468.64 |
| 30 | 6-CF$_3$ | — | 3-Cl | 2-S | 4- | S | —OC$_2$H$_5$ | —OC$_2$H$_5$ | A | n 25/d = 1.5560 |
| 31 | — | 6-Cl | — | 2-S | 2- | S | —OC$_2$H$_5$ | —OC$_2$H$_5$ | A | n 25/d = 1.5856 |
| 32 | — | 6-F | — | 2-S | 2- | S | —OC$_2$H$_5$ | —OC$_2$H$_5$ | A | n 25/d = 1.5716 |
| 33 | — | 3-Cl | — | 2-S | 2- | S | —OC$_2$H$_5$ | —OC$_2$H$_5$ | A | n 25/d = 1.5953 |
| 34 | 6-CF$_3$ | — | — | 2-S | 2- | S | —OC$_2$H$_5$ | —OC$_2$H$_5$ | A | M.W. = 423.28 |
| 35 | 6-CF$_3$ | — | — | 2-SO$_2$ | 4- | S | —OC$_2$H$_5$ | —OC$_2$H$_5$ | A | n 25/d = 1.5283 |
| 36 | 6-CF$_3$ | — | 3-F | 2-S | 4- | S | —OC$_2$H$_5$ | —OC$_2$H$_5$ | A | M.W. = 441.26 |
| 37 | — | 2,3,5-Cl | — | 4-S | 2- | S | —OC$_2$H$_5$ | —OC$_2$H$_5$ | A | n 25/d = 1.6063 |
| 38 | — | 3,5,6-Cl | — | 2-S | 2- | S | —OC$_2$H$_5$ | —OC$_2$H$_5$ | A | n 25/d = 1.6121 |
| 39 | — | — | — | 2-S | 4- | S | —OC$_2$H$_5$ | —OC$_2$H$_5$ | A | n 25/d = 1.5799 |
| 40 | 4-SO$_2$C$_2$H$_5$ | — | — | 2-S | 4- | S | —OCH$_3$ | —OCH$_3$ | A | M.W. = 419.46 |
| 42 | 6-OCH$_3$ | — | — | 2-S | 2- | S | —OC$_2$H$_5$ | —OC$_2$H$_5$ | A | n 25/d = 1.5645 |
| 43 | — | 3,6-Cl | — | 2-S | 2- | S | —OC$_2$H$_5$ | —OC$_2$H$_5$ | A | M.W. = 424.18 |
| 44 | — | 6-F | — | 2-SO | 4- | S | —OC$_2$H$_5$ | —OC$_2$H$_5$ | A | n 25/d = 1.5588 |
| 45 | — | 6-F | — | 2-SO$_2$ | 4- | S | —OC$_2$H$_5$ | —OC$_2$H$_5$ | A | n 25/d = 1.5594 |
| 46 | — | 6-Cl | — | 2-S | 2- | S | —OCH$_3$ | —OCH$_3$ | A | M.W. = 361.70 |
| 47 | — | 6-F;3,5-Cl | — | 2-S | 2- | S | —OC$_2$H$_5$ | —OC$_2$H$_5$ | A | n 25/d = 1.60 |
| 49 | 5-SC$_2$H$_5$ | — | — | 2-S | 2- | O | —OCH$_3$ | —OCH$_3$ | A | M.W. 371.26 |
| 50 | — | — | — | 4-S | 4- | S | —OC$_2$H$_5$ | —OC$_2$H$_5$ | A | n 25/d = 1.6123 |
| 51 | 6-CF$_3$ | — | — | 2-S | 4- | S | —OCH$_3$ | —OCH$_3$ | A | n 25/d = 1.5577 |
| 52 | 6-CF$_3$ | — | — | 2-S | 4- | O | —OC$_2$H$_5$ | —OC$_2$H$_5$ | A | n 25/d = 1.5226 |
| 53 | 6-OP(S)(OC$_2$H$_5$)$_2$ | 3,5-Cl | — | 2-S | 4- | S | —OC$_2$H$_5$ | —OC$_2$H$_5$ | B | n 25/d = 1.5768 |
| 54 | 6-CF$_3$ | — | — | 2-S | 4- | S | —OC$_2$H$_5$ | —NHC$_2$H$_5$ | A | n 25/d = 1.5550 |
| 55 | 6-CF$_3$ | — | — | 2-SO | 4- | S | —OC$_2$H$_5$ | —OC$_2$H$_5$ | A | n 25/d = 1.5345 |
| 56 | 6-CF$_3$ | — | — | 2-S | 4- | O | —OCH$_3$ | —OCH$_3$ | A | n 25/d = 1.5303 |
| 57 | 6-CF$_3$ | — | — | 2-O | 4- | S | —OCH$_3$ | —OCH$_3$ | A | n 25/d = 1.5224 |
| 58 | 6-CF$_3$ | — | — | 2-O | 4- | O | —OC$_2$H$_5$ | —OC$_2$H$_5$ | A | n 25/d = 1.4899 |
| 59 | — | 6-Cl | — | 2-O | 4- | S | —OCH$_3$ | —OCH$_3$ | A | n 25/d = 1.5792 |
| 60 | — | 6-Cl | — | 2-O | 4- | O | —OC$_2$H$_5$ | —OC$_2$H$_5$ | A | n 25/d = 1.5317 |
| 61 | — | 6-Cl | — | 2-O | 4- | O | —OCH$_3$ | —OCH$_3$ | A | n 25/d = 1.4980 |
| 62 | 6-CF$_3$ | — | — | 2-O | 4- | O | —OCH$_3$ | —OCH$_3$ | A | M.W. = 363.12 |
| 63 | 6-CF$_3$ | — | — | 2-O | 4- | O | —N(CH$_3$)$_2$ | —N(CH$_3$)$_2$ | A | n 25/d = 1.5098 |
| 64 | 6-CF$_3$ | — | — | 2-O | 4- | S | —OCH$_3$ | —OCH$_3$ | A | n 25/d = 1.5730 |
| 65 | — | 6-Cl | — | 2-O | 4- | S | —OCH$_3$ | —OCH$_3$ | A | n 25/d = 1.6234 |
| 66 | — | 6-F | — | 2-S | 4- | S | —OCH$_3$ | —OCH$_3$ | A | n 25/d = 1.6386 |
| 67 | — | 2,3,5,6-F | — | 4-S | 4- | O | —NHCH$_3$ | —NHCH$_3$ | A | M.W. = 381.20 |
| 68 | — | 6-F | — | 2-O | 4- | O | —OC$_2$H$_5$ | —OC$_2$H$_5$ | A | n 25/d = 1.5031 |
| 69 | — | 6-F | — | 2-O | 4- | S | —OCH$_3$ | —OCH$_3$ | A | n 25/d = 1.5568 |
| 70 | 6-CF$_3$ | — | — | 2-O | 4- | S | —N(CH$_3$)$_2$ | —N(CH$_3$)$_2$ | A | N.W. = 438.25 |
| 71 | — | 6-F | — | 2-O | 4- | O | —OCH$_3$ | —OCH$_3$ | A | n 25/d = 1.5262 |
| 72 | 4-OP(O)(NHCH$_3$)$_2$ | — | — | 2-O | 4- | O | —NHCH$_3$ | —NHCH$_3$ | B | M.W. = 415.14 |
| 73 | 4-OP(S)(NHCH$_3$) | — | — | 2-O | 4- | S | —NHCH$_3$ | —NHCH$_3$ | B | M.W. = 541.36 |
| 74 | 6-SP(S)(OCH$_3$)$_2$ | 3,5-Cl | 3-Cl | 2-O | 4- | S | —OCH$_3$ | —OCH$_3$ | B | M.W. = 570.83 |
| 75 | 6-OP(S)(N(CH$_3$)$_2$)$_2$ | 3,5-F | 4-Cl | 2-O | 3- | S | —N(CH$_3$)$_2$ | —N(CH$_3$)$_2$ | B | M.W. = 572.73 |

TABLE I-continued

| Compound No. | D | X | X' | Z | O | G | R | R' | Method of Preparation | Physical[a] Properties |
|---|---|---|---|---|---|---|---|---|---|---|
| 76 | — | 6-Br;3,5-F | 4-F | 2-O | 3- | O | —OCH$_3$ | —OCH$_3$ | A | M.W. = 410.02 |
| 77 | 6-CF$_3$ | — | — | 2-SO | 4- | O | —OC$_2$H$_5$ | —OC$_2$H$_5$ | A | n 25/d = 1.5785 |
| 78 | 6-CF$_3$ | — | — | 2-SO | 4- | S | —OCH$_3$ | —OCH$_3$ | A | M.P. = 70° – 73° C |
| 79 | 6-CF$_3$ | — | — | 2-SO$_2$ | 4- | O | —OC$_2$H$_5$ | —OC$_2$H$_5$ | A | n 25/d = 1.5080 |
| 80 | 6-CF$_3$ | — | — | 2-SO$_2$ | 4- | O | —OCH$_3$ | —OCH$_3$ | A | M.P. = 51° – 54° C |
| 81 | 6-SO$_2$CH$_3$ | — | — | 2-S | 4- | O | —OC$_2$H$_5$ | —OC$_2$H$_5$ | A | n 25/d = 1.5663 |
| 82 | 6-SO$_2$CH$_3$ | — | — | 2-S | 4- | S | —OC$_2$H$_5$ | —OC$_2$H$_5$ | A | n 25/d = 1.5846 |
| 83 | 6-SO$_2$CH$_3$ | — | — | 2-S | 4- | S | —OCH$_3$ | —OCH$_3$ | A | n 25/d = 1.5970 |
| 84 | — | 2,3,5,6-Cl | — | 4-S | 4 | S | —OCH$_3$ | —OCH$_3$ | A | M.W. = 465.08 |

[a] M.W. = Molecular Weight; M.P. = Melting Point

Preparation of Starting Materials

The pyridyloxyphenols employed as starting materials can be prepared by a variety of methods. For example those compounds wherein the pyridine ring is substituted (D) by either cyano, nitro, trifluoromethyl, loweralkyl, or loweralkylthio can be prepared by reacting equimolar amounts of an appropriately substituted halopyridine with an appropriately substituted methoxyphenol in the presence of a solvent and a base such as, for example, an alkali metal hydroxide or carbonate followed by the treatment of this intermediate product, with or without prior separation of the intermediate product, under reflux conditions with concentrated hydrobromic acid.

This two-step preparation procedure can be characterized by the following

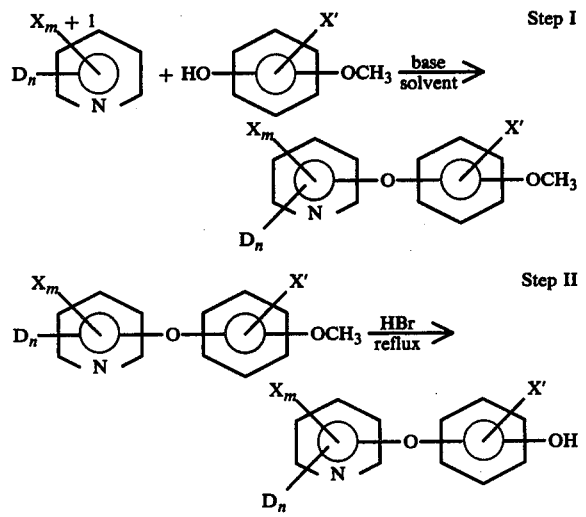

wherein X, X', m and n are as hereinabove set forth and D is as set forth in the above paragraph.

The above reactions are conveniently carried out by contacting the reactants together in a solvent such as, for example, monoglyme, hexamethylphosphoramide, acetonitrile, dimethylformamide or mixtures thereof and in the presence of a base such as, for example, sodium or potassium hydroxide or sodium or potassium carbonate. The reaction takes place smoothly at atmospheric pressure and temperatures between about 0° and the reflux temperature of the reaction mixture and is conveniently carried out at room temperature.

In carrying out the reaction, the reactants are contacted together in at least equimolar proportions of the pyridine to the phenol reactant. It is preferred, however, to employ a slight (~ 10 percent) excess of the phenol reactant. The base is usually employed in an amount of from about 1.0 to about 1.5 moles per mole of the phenol reactant. The reactants are maintained under the aforedescribed conditions until the reaction is substantially complete, usually from about 1 to about 24 hours.

If it is desired to recover the intermediate from the first step, the reaction mixture is diluted with water and extracted with a solvent such as, for example, methylene chloride, hexane, benzene, chloroform or carbon tetrachloride. The solvent extract is washed with a dilute basic solution and/or water and dried and the solvent removed by evaporation under reduced pressure leaving the desired product as a residue.

The starting pyridyloxyphenols wherein the pyridine ring is substituted (D) with a loweralkoxy, or hydroxy group can be prepared by reacting at least equimolar amounts of a polyhalopyridine with an appropriately substituted methoxyphenol in the presence of a solvent and a base. The solvents, base and reaction conditions are the same as outlined hereinabove for Step I. The product of this reaction is thereafter refluxed with concentrated hydrobromic acid and thereafter reacted under reflux with an excess of an appropriate alkali metal loweralkoxide in the presence of (1) the corresponding loweralkanol to produce the desired product wherein (D) is loweralkoxy; or (2) an alkali metal hydroxide to produce the desired product wherein (D) is hydroxy. These reactions can be characterized as follows:

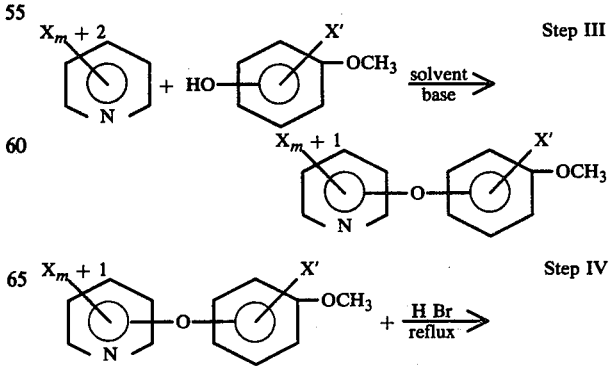

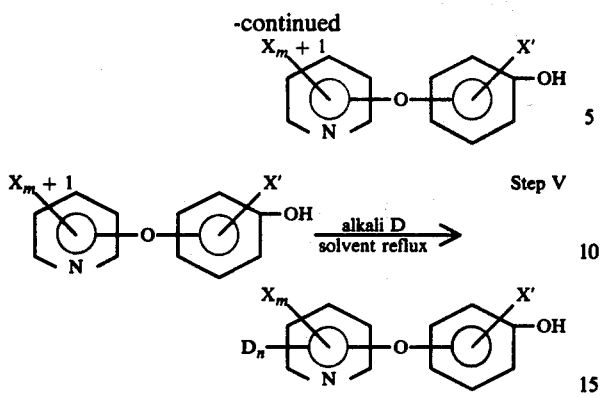

Step V wherein X, X', m and n are as set forth hereinabove and D is as set forth in this paragraph.

The ((pyridyl)thio)phenol starting material wherein D is cyano, nitro, trifluoromethyl, loweralkyl, loweralkylsulfonyl, or loweralkylthio can be prepared in a one step operation wherein equimolar amounts of an appropriately substituted halopyridine is reacted with an appropriately substituted mercapto phenol in the presence of a solvent and a base. The solvent, base and reaction conditions are the same as set forth above in Step I.

This reaction can be characterized as follows:

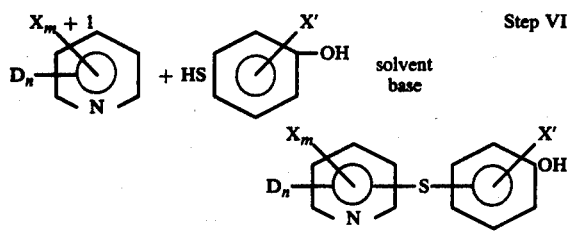

Step VI wherein X, X', D, m and n are as set forth in the paragraph directly hereinabove.

The product is recovered from the reaction mixture by first filtering the reaction mixture to remove any solid reaction by-products present. The filtrate is thereafter concentrated by solvent evaporation and the residue is mixed with an aqueous dilute basic solution followed by washing with a solvent such as, for example, methylene chloride, hexane, benzene, chloroform or carbon tetrachloride. The aqueous solution is acidified with a concentrated mineral acid and the solid product which precipitates is recovered by filtration, water washed and dried.

Those ((pyridyl)thio)phenol starting materials wherein the pyridine ring is substituted (D) with a loweralkoxy or hydroxy group can be prepared by reacting equimolar amounts of a polyhalopyridine with an appropriately substituted mercapto phenol following the procedure set forth above for reaction Step VI. The product of this reaction is thereafter reacted under reflux with an excess of an appropriate alkali metal alkoxide, in the presence of the corresponding alcohol or alkali metal hydroxide to obtain the corresponding loweralkoxy, or hydroxy product. These reactions can be characterized as follows:

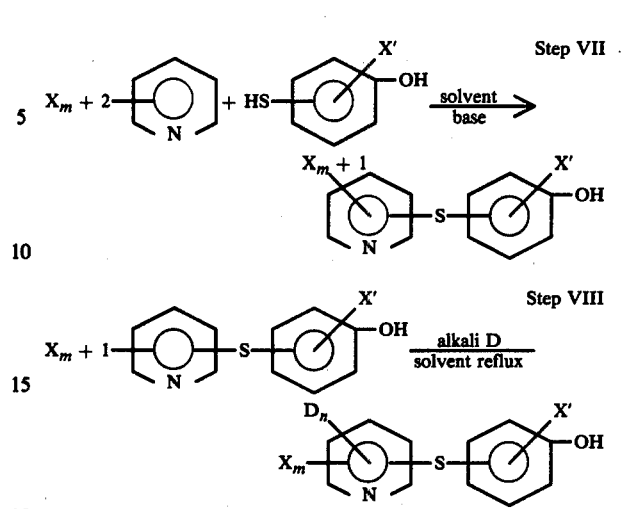

wherein X, X', D, m and n as set forth hereinabove in this paragraph.

The ((pyridyl)sulfinyl- and sulfonyl)phenols employed as starting materials can be prepared by the conventional oxidation of the corresponding ((pyridyl)thio)phenol with hydrogen peroxide in the presence of a reaction medium such as active acid. The oxidation of one molecule of the ((pyridyl)thio)phenol to the corresponding ((pyridyl)-sulfinyl)phenol or the oxidation of one molecule of the ((pyridyl)sulfinyl)phenol to the corresponding ((pyridyl)sulfonyl)phenol requires one atom of oxygen for each molecule of the sulfur compound to be oxidized. The oxidation of the ((pyridyl)thio)phenol directly to the corresponding sulfonyl compound, on the other hand, consumes two atoms of oxygen for each molecule of the sulfur compound so oxidized.

In carrying out the various oxidation reactions to prepare the sulfonyl compounds of the present inventions, it is preferable to employ an excess of the oxidizing agent, whereas in preparing the sulfinyl compounds, it is preferable not to provide oxygen appreciably in excess of the stoichiometric quantities consumed in the conversion and to employ milder reaction conditions.

Generally, the oxidation reactions take place at temperatures of from about 75° to about 120° C. In a convenient method, the reaction is carried out at the boiling temperature of the reaction mixture and under reflux. In carrying out the reaction, the reactants are contracted in any order or fashion, and preferably in amounts stoichiometric for the preparation of the desired product. The reaction mixture is then maintained at a temperature within the reaction temperature range until the desired degree of conversion is achieved. Following the reaction period, the product can be separated by conventional procedures such as evaporation of the reaction medium to obtain the product as a solid residue. In an alternative procedure, the reaction mixture is washed with cold water and is thereafter filtered, centrifuged or the like to obtain the crystalline product.

The following examples illustrate the preparation of representative starting materials.

EXAMPLE V

2-Trifluoromethyl-6-(4-methoxyphenoxy)pyridine

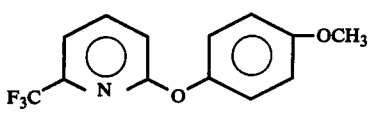

A mixture comprising 90.5 grams (0.5 mole) of 2-chloro-6-trifluoromethylpyridine, 65 grams (0.55 mole) of 4-methoxyphenol and 36.4 grams (0.55 mole) of 85 percent potassium hydroxide was stirred in 1 liter of a 1:1 mixture of monoglyme and hexamethylphosphoramide for 1 hour at room temperature and thereafter heated overnight at reflux. The resulting mixture was diluted with water and extracted with hexane. The hexane extract was washed with a dilute sodium hydroxide solution followed by water washing. The extract was dried and concentrated under reduced pressure to give 127 grams (94 percent of theoretical) of 2-trifluoromethyl-6-(4-methoxyphenoxy)pyridine.

EXAMPLE Va

4((-6-Trifluoromethyl-2-pyridyl)oxy)phenol

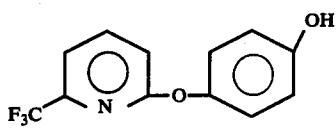

A mixture comprising 127 grams of 2-trifluoromethyl-6-(4-methoxyphenoxy)pyridine, prepared above in Example V, and 250 milliliters of 48 percent hydrobromic acid was heated at reflux overnight. The mixture was cooled and diluted with water and thereafter extracted with methylene chloride. The extract was concentrated under reduced pressure leaving the 4-((6-trifluoromethyl-2-pyridyl)oxy)phenol, a white solid, as a residue. Recrystallization of this solid from a 3:1 mixture of benzene and hexane gave 69.1 grams (57 percent of theoretical) of the product as a white crystalline solid which melted at 94°–95° C.

EXAMPLE VI

4((6-Fluoro-2-pyridyl)thio)phenol

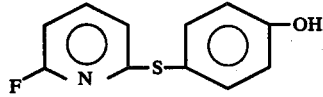

A mixture comprising 69 grams (0.6 mole) of 2,6-difluoropyridine, 75.6 grams (0.6 mole) of 4-mercaptophenol and 49.5 grams (0.75 mole) of 85 percent potassium hydroxide was stirred in 300 milliliters of monoglyme for ~ 4 days at room temperature. At the end of this time, the reaction mixture was filtered to remove any solid by-products present. The filtrate was concentrated to remove most of the monoglyme and the residue mixed with 400 milliliters of 5 percent sodium hydroxide. The mixture was washed with methylene chloride and the aqueous solution acidified with concentrated hydrochloric acid. The solid 4-((6-fluoro-2-pyridyl)thio)phenol product precipitated out and was recovered by filtration, washed with water and dried.

The product was recovered in a yield of 112 grams (87 percent of theoretical) and melted at 123°–124° C.

EXAMPLE VII 4-((6-Methoxy-2-pyridyl)thio)phenol

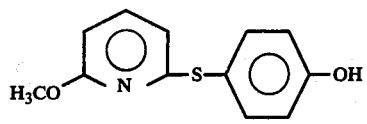

A solution of 11.05 grams (0.05 mole) of 4-((6-fluoro-2-pyridyl)thio)phenol (prepared as above in Example VI) and 8.10 grams (0.15 mole) of sodium methoxide in 200 milliliters of methanol was heated at reflux overnight. The resulting solution was acidified with concentrated hydrochloric acid and thereafter diluted with water. The solid 4-((6-methoxy-2-pyridyl)thio)phenol product was recovered by filtration, water washed and dried. The product was recovered in a yield of 10 grams (86 percent of theoretical) and melted at 88.5°–94.5° C.

EXAMPLE VIII

4((6-hydroxy-2-pyridyl)thio)phenol

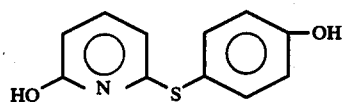

A solution of 5 grams (0.023 mole) of 4-((6-fluoro-2-pyridyl)thio)phenol and 2.72 grams (0.68 mole) of sodium hydroxide in 15 milliliters of water was heated at reflux for 2½ hours. The resulting solution was poured over a mixture of ice and methylene chloride and the resulting mixture was vigorously stirred. The mixture was acidified by the dropwise addition of concentrated hydrochloric acid. The white crystalline solid 4-((6-hydroxy-2-pyridyl)thio)phenol product which precipitated out was recovered by filtration and washed with methylene chloride. The product was recovered in a yield of 4.35 grams (88 percent of theoretical) and melted at 234°–238° C.

EXAMPLE IX

2-Chloro-6-(4-methoxyphenoxy)pyridine

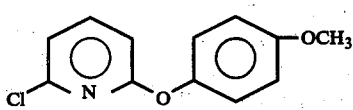

A solution comprising 14.8 grams (0.1 mole) of 2,6-dichloropyridine, 12.4 grams (0.1 mole) of 4-methoxyphenol and 8.4 grams (0.15 mole) of flake potassium hydroxide in 100 milliliters of a 1:1 mixture of monoglyme and hexamethylphosphoramide was stirred for 24 hours at room temperature. The resulting mixture was diluted with water and thoroughly extracted with hexane. The extract was washed with water, dried and concentrated under reduced pressure. The residue was recrystallized from pentane giving 14.5 grams (64 percent of theoretical) of 2-chloro-6-(4-methoxyphenoxy)-pyridine which melted at 63°–65° C.

EXAMPLE X

4((6-Chloro-2-pyridyl)oxy)phenol

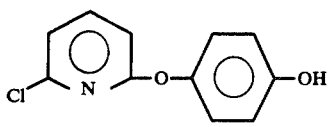

A mixture of 11 grams of 2-chloro-6-(4-methoxyphenoxy)pyridine, prepared above in Example IX and 100 milliliters of 48 percent hydrobromic acid was heated at reflux overnight. The reaction mixture was cooled and diluted with water. The 4-((6-chloro-2-pyridyl)oxy)phenol separated out as a yellow crystalline solid which was isolated by filtration. The product was recovered in a yield of 10 grams (97 percent of theoretical) and melted at 125°–130° C.

The substituted phosphorochloridates employed as starting materials are all known compounds which can be obtained commercially and are prepared in the known prior art including the field of patent literature.

The compounds of the present invention are useful as insecticides in a variety of household, industrial, and agricultural operations. In particular, the compounds of the present invention can be employed to give a quick inactivation of insect organisms; this is spoken of as a "quick knockdown." Also, the subject compounds exhibit residual activity over long periods of time following utilization in areas such as, wood or wood products, fabrics, metal or metallic materials, plastic materials, and the like. Because of this excellent residual activity and because of the "quick knockdown," the subject compounds are particularly suitable for the control, inside houses, barns, warehouses, public buildings, and the like, of pests, including cockroaches, such as the German cockroach, American cockroach, and brown-banded cockroach; beetles, such as the black-carpet beetle, confused flour beetle, saw-tooth grain beetle, and larder beetle; spiders, silverfish; bedbugs; fleas, such as those on bedding used by household pets, and flea larvae; mosquitos; boxelder bugs; spiders; mites; ants; centipedes; and flies, such as the common housefly. The subject compounds are highly effective for such indoor control of insect pests and thus are particularly adapted for such employment.

The new organophosphorus compounds of the present invention are also very effective for the control of the many insect pests found on the roots or aerial portions of growing plants, including aphids, mites, plant pathogens, and chewing and sucking insects, such as Southern army worm (*Prodenia eridania*), two-spotted spider mite (*Tetranychus bimaculatus*), cotton aphid (*Aphis gossypii*), cabbage looper (*Trichoplusia ni*), bollworm (*Heliothis armigera*), codling moth (*carpocapsa pomonella*), beet armyworm (*Laphygma exigua*) and western spotted cucumber beetle (*Diabrotica undecimpunctata*).

In contrast with the excellent residual activity of the subject compounds in contact with essentially inert objects, the subject compounds, when applied to plants, plant parts, and their habitats to protect the plants from the attack of insect pests, exhibit residual control of the insects over only a relatively brief period of time.

The new compounds can also be included in inks, adhesives, soaps, polymeric materials, cutting oils or in oil or latex paints. Also, the present compounds can be distributed in textiles, cellulosic materials, or in grains, or can be employed in the impregnation of wood and lumber. Additionally, they can be applied to seeds. In yet other procedures, the organophosphorus compounds can be vaporized or sprayed or distributed as aerosols into the air, or onto surfaces in contact with the air. In such applications, the compounds manifest the useful properties hereinbefore described.

The methods of the present invention comprise contacting an insect with an insecticidally effective or inactivating amount of one of the present organophosphorus compounds. Contacting can be effected by application of the compound to the habitat of the insects. Representative habitats include soil, air, water, food, vegetation, inert objects, stored matter such as grains, other animal organisms, and the like. The inactivation can be lethal, immediately, or with delay, or can be a sub-lethal one in which the inactivated insect is not able to carry out one or more of its normal life processes. This latter situation prevails when one of the systems of the insect, typically the nervous system, is seriously disturbed. A preferred embodiment of the present invention comprises the employment of the present method for the kill and control of insects; such employment gives excellent results, particularly in control of insects that have developed resistance against other pest-control substances.

The inactivation of an insect by the application of an insecticidally effective or inactivating amount of one of the phosphorus compounds is critical to the method of the present invention. The phosphorus compound can sometimes be employed in unmodified form. Frequently, however, the desirable properties of such compound can be utilized only when the compound is modified by the employment with it of a pesticidal adjuvant. Thus, for example, the present compounds are of very low solubility in water but are relatively soluble in oils, including plant essential oils. Therefore, the practical enjoyment of the beneficial utilities of the present compounds often requires that the compound be composited with one or more pesticidal adjuvant substances, and the resulting compositions are comprehended within the present invention.

The composition can be in the form of a liquid or a dust; and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the phosphorus compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising one or more of the phosphorus compounds, an organic liquid as a solvent and carrier therefor, and a propellant material. Numerous other embodiments will become available to those skilled in the art in view of the teachings set forth hereinbelow.

The exact concentration of the phosphorus compounds in a composition thereof with an adjuvant therefor can vary; it is only necessary that the phosphorus compounds be present in a sufficient amount so as to make possible the application of an insecticidally effective or inactivating dosage. Generally, for practical applications, the active phosphorus compounds can be broadly applied to insect pest organisms or their habitat in compositions containing from about 0.00001 percent to about 98 percent by weight of the phosphorus compound.

When combining the present toxicants with adhesives, detergents, cutting oils, paints, polymeric materials, textiles, paper, and other similar products, good results are obtained when the compounds are incorporated in such products in the amount of 0.005 to 0.1 percent by weight, and when heavier applications are needed in the amount of from 0.1 to 2.0 percent by weight. When one or more than one of the present toxicants is combined with wood, excellent results are obtained when the toxicant compound or compounds are incorporated by conventional treatment of the wood in the amount of from 0.00005 to 0.05 pound per cubic foot of wood, depending on depth of penetration, exposure, and the like.

In the preparation of dust compositions, the phosphorus product can be compounded with any of the finely divided carrier solids such as pyrophyllite, diatomaceous earth, gypsum and the like. In such operations, the finely divided carrier is ground or mixed with one or more of the phosphorus compounds, as active agent, or wetted with a solution of the active agent in a volatile organic solvent. Similarly, dust compositions containing the phosphorus product can be similarly compounded from various of the solid dispensing agents, such as fuller's earth, attapulgite and other clays. These dust compositions can be employed as treating compositions or can be employed as concentrated and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, one of the phosphorus compounds or a dust concentrate composition containing such compound can be incorporated in intimate mixture with surface active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the phosphorus product can be compounded with a suitable water-immiscible organic liquid and surface active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the non-ionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, the phosphorus product or a composition containing the product is applied to the insects to be controlled directly, or by means of application to a portion or portions of their habitat in any convenient manner, for example, by means of hand dusters or sprayers or by simple mixing with the food to be ingested by the organisms. Application to the foliage of plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane. The present invention also comprehends the employment of compositions comprising one of the phosphorus compounds, an adjuvant, and one or more other biologically active materials, such as insecticides, fungicides, miticides, bactericides, nematocides, and the like.

A preferred and especially convenient matter for the application of one or more of the present product comprises the use of a self-pressurized back formulation which can be used, for example, as a space or surface spray. Such a formulation can comprise one or more of the phosphorus compounds, an organic liquid as a solvent and vehicle therefor, and a propellant material which can be a condensed and compressed gas or a substance which, at room temperature, is a gas under atmospheric pressure but which liquifies under superatmospheric pressure. Where the propellant material is of the latter type, the self-pressurized pack formulation is often spoken of as an aerosol. Representative propellants include propane, butane, nitrogen, and the fluorinated hydrocarbons, such as dichlorodifluoromethane and trichlorofluoromethane. Generally, the propellant constitutes from 25 to 95 percent by weight of the total self-pressurized pack. As vehicle, there can be employed any liquid in which the desired amount of product is capable of being dispersed; preferred vehicles include petroleum distillates, kerosene, and methylene chloride. The self-pressurized pack formulation can also include other materials, such as other biologically active agents or synergists. For further discussion of the use of self-pressurized pack formulations, see U.S. Pat. No. 1,892,750 and 2,321,023.

The compositions of the present invention will be illustrated in further detail below with reference to the examples, but the kinds and mixing proportions of compounds and additives are not limited to those shown in the examples but are variable within wide ranges. In Examples 11–27, the compounds employed are referred to by the compound number as herein above set forth. All parts are based on weight percent of the total composition.

EXAMPLE XI

A dust composition is prepared by admixing and pulverizing 3 parts of one of the compounds numbered 2, 3, 4, 8, 10, 17, 20, 23 or 27 with 97 parts of Barden clay to obtain a composition containing 3 percent of the active ingredient. In application, the composition is dusted as such.

EXAMPLE XII

50 Parts of compound number (7), 5 parts of a wetting agent (alkylbenzenesulfonate type) and 45 parts of diatomaceous earth are thoroughly pulverized and mixed together to obtain a wettable powder containing 50 percent of active ingredient. In application, the powder is diluted with water and used as a spray.

EXAMPLE XIII

A mixture of 5 parts of one of the compounds numbered 2, 5, 7, 13, 18 or 25; 93.5 parts of clay and 1.5 parts of polyvinyl alcohol are thoroughly kneaded with water and the mixture granulated and dried. The granule composition contains 5 percent of the active ingredient and can be applied as such.

EXAMPLE XIV

25 Parts of compound numbered 59, 50 parts of toluene and 25 parts of Atlox 3404F ® (proprietary material of Imperial Chemical Industries, U.S. which is a polyoxyethylene alkyl aryl ether-alkyl aryl sulfonate blend) are mixed together to obtain an emulsifiable concentrate having an active ingredient concentration of 25 percent. In application, the concentrate is diluted with water and sprayed.

EXAMPLE XV 7.6 Parts of one of the compounds numbered 17, 20, 27, 35, 50, 55, 59 or 67; 80.4 parts of purified xylene and 12.0 parts of Atplus 300F ® (a proprietary material of Imperial Chemical Industries, U.S. which is a polyoxyethylene sorbitol ester) are mixed together to obtain an emulsifiable concentrate having an active ingredient concentration of 7.6%. In application, the preparation is diluted with water and used as a spray.

EXAMPLE XVI

1 Part of one of the compounds numbered 72, 73, 74, 75, 80 or 84 is mixed with 99 parts of purified Kerosene to obtain an oil preparation having an active ingredient concentration of 1 percent. In application, the composition can be atomized or sprayed as is.

The control of pest organisms by the contacting thereof with one or more of the phosphorus compounds of the present invention is illustrated by the following examples.

EXAMPLE XVII

To a standard poultry feed was added one of the test compounds hereinbefore numbered 5, 15 or 16 at a predetermined concentration of the test compound per million parts of the ultimate mixture. Two week old chickens (chicks) were fed diets containing one of the above compounds. At the same time chicks of the same age and past history were fed the same diets containing no test compounds to serve as controls.

After 5 days on the diet, fecal samples are collected from the chicks and placed in 4-6 ounce containers. Each fecal sample was inoculated with 50-100 infective common housefly eggs (*Musca domestica*) and the eggs were washed into the sample with 20 milliliters of a mold-inhibitor solution. The containers were sealed except for an air hole (to allow air to reach the eggs) and the samples were held at 95° F. and 80 percent relative humidity for three (3) days. At the end of this period, the samples were examined for the presence or absence of active fly larvae. The results of this examination are set forth hereinbelow in Table II.

TABLE II

| Compound number | Amount of active compound in diet | Percent kill and control of fly larvae |
|---|---|---|
| 5 | 500 | 100 |
| 15 | 250 | 99 |
| 16 | 62 | 100 |
| Control | — | 0 |

EXAMPLE XVIII

Containers are prepared each containing 20 grams of calf feces. Predetermined amounts of one of the compounds numbered 5, 6, 8, 9 and 30 were blended with the feces. 15 Grams of the resulting mixture was inoculated with viable egg of the common house fly (*Musca domestica*). At the same time feces containing no test compound were also inoculated to serve as controls. The containers were maintained at room temperature for 48 hours, after which they were examined to determine the presence or absence of fly larvae. The results of this examination are set forth below in Table III.

TABLE III

| Test Compound number | Concentration in PPM* of the test Compound | Percent Kill and control of fly larvae |
|---|---|---|
| 5 | 100 | 100 |
|  | 10 | 100 |
|  | 1.0 | 100 |
| 6 | 100 | 100 |
| 8 | 100 | 100 |
|  | 10 | 100 |
|  | 1.0 | 100 |
| 9 | 100 | 100 |
| 30 | 50 | 100 |
| Control | — | 0 |

*PPM = parts of test compound per million parts of the total admixture

EXAMPLE XIX

One of the test compounds numbered 16 and 41 is administered orally to white mice by means of a blunt hypodermic needle with a one (1) cubic centimeter syringe. The compounds were prepared for administration by mixing a predetermined amount of the test compound with a predetermined amount of silica gel. The dry mixture was thereafter diluted to the desired concentration with a predetermined amount of a 50:50 acetone-water mixture. At the same time, additional mice were treated in the same manner with a mixture containing no active material to serve as controls. After all of the mice were treated, ten (10) stable flies (*Stomoxys calcitrans*) were allowed to feed on each of the mice for one hour. At the completion of this feeding period, the flies were separated. After a period of 24 hours the percent mortality of the flies was determined and the results thereof are set forth below in Table IV.

TABLE IV

| Test Compound Number | Concentration In Milligram per Kilogram of body weight of test compound | Percent Mortality of Stable flies |
|---|---|---|
| 16 | 100 | 100 |
| 41 | 100 | 100 |
| Control | — | 0 |

EXAMPLE XX

Predetermined amounts of one of the compounds hereinafter set forth, in the form of a silica gel admixture, was mixed with predetermined amounts of acetone. The solutions thus prepared were absorbed onto cotton rolls, produced as No. 2 dental plugs. At the same time additional rolls were treated with silica gel and acetone, alone to serve as controls. The rolls were three-fourth inch long and 2 such rolls were placed side by side in 0.625 ounce (5 dram) glass vials. The treated rolls were allowed to air dry for 24 hours so that the acetone could evaporate off. One cubic centimeter of bovine serum was placed on the cotton rolls in each vial. Thereafter, 50–100 1st stage copper bottle fly maggots of 1–6 hours of age were placed on the rolls in each vial. The vials were plugged with cotton and held for 24 hours at 82°–84° F. and 80 percent relative humidity. At the end of this period, the vials were examined to determine the percent kill and control of the maggots. The results of this examination are set forth below in Table V.

TABLE V

| Compound Number | Concentration in PPM of active compound employed | Percent Kill and control of maggots |
|---|---|---|
| 1 | 10 | 100 |
| 2 | 10 | 100 |
| 3 | 10 | 100 |
| 5 | 10 | 100 |
|  | 1.0 | 100 |
|  | .50 | 100 |
|  | .25 | 100 |
|  | .13 | 100 |
| 6 | 10 | 100 |
|  | 1.0 | 100 |
| 8 | 10 | 100 |
|  | 1.0 | 100 |
|  | .50 | 100 |
| 9 | 10 | 100 |
|  | 1.0 | 100 |
|  | .50 | 100 |
|  | .25 | 100 |
| 11 | 10 | 100 |
| 13 | 10 | 100 |
| 14 | 10 | 100 |
| 15 | 10 | 100 |
| 20 | 10 | 100 |
| 29 | 10 | 100 |
| 30 | 10 | 100 |
|  | 1.0 | 100 |
| 31 | 10 | 100 |
| 35 | 10 | 100 |
| 39 | 10 | 100 |
| 44 | 10 | 100 |
| 45 | 10 | 100 |
| 46 | 10 | 100 |
| 51 | 10 | 100 |
| 52 | 10 | 100 |
| 53 | 10 | 100 |
| 54 | 10 | 100 |
| 55 | 10 | 100 |
| Control | — | 0 |

EXAMPLE XXI

Cylindrical cages about 3⅜ inches in diameter by 3¼ inches high were fitted with wire screen on the top and bottom. Into each cage was placed a predetermined number of German cockroaches. An aqueous dispersion prepared by admixing one of the hereinafter set forth compounds with a predetermined amount of water and a surfactant was sprayed on the cockroaches through the screen from a distance of about 15 inches. At the same time additional cockroaches were sprayed with a water-surfactant mixture containing no active toxicant to serve as controls. After spraying, the cockroaches were fed a sugar-water diet for 3 days. At the end of this period, the cages were examined to determine the percent mortality present in each cage. The results of this examination are set forth below in Table VI.

TABLE VI

| Compound Number of active compound | Concentration of active compound in PPM | Percent mortality of cockroaches |
|---|---|---|
| 2 | 400 | 30 |
| 3 | 400 | 100 |
| 8 | 400 | 80 |
| 11 | 400 | 80 |
| 13 | 400 | 100 |
| 34 | 400 | 100 |
| 45 | 400 | 100 |
| 56 | 400 | 83 |
| Control | — | 0 |

EXAMPLE XXII

Following the test procedure outlined in Example 21 and employing Southern house mosquito adults as the target insect, the results set forth below in Table VII were obtained.

TABLE VII

| Compound Number | Concentration in PPM of active compound | Percent mortality of Mosquito adults |
|---|---|---|
| 1 | 12.0 | 75 |
| 5 | 12.0 | 100 |
|  | 3.0 | 100 |
|  | .70 | 80 |
| 6 | 12.0 | 70 |
| 8 | 12.0 | 100 |
|  | 3.0 | 100 |
|  | .70 | 100 |
| 9 | 12.0 | 80 |
| 11 | 12.0 | 80 |
| 13 | 12.0 | 100 |
| Control | — | 0 |

EXAMPLE XXIII

Containers containing a predetermined amount of water were treated with one of the test compounds hereinafter set forth in the form of an aqueous dispersion. The test compounds were added to the water in a quantity sufficient to have the compound present at a predetermined dilution. A predetermined number of Southern House Mosquito larva were added to each container. At the same time control containers were also prepared. At the end of 3 days, the containers were examined to determine the percent kill and control of the larvae and the results of this examination showed that each of the following compounds gave 100 percent kill and control of the larvae at a concentration of 1 part of the compound per million parts of the ultimate aqueous mixture. These compounds were compounds numbered 1–6, 8–11, 13–16, 19–26, 29–33, 35, 37–39, 42, 43, 45–47 and 50–55. The control mosquitos remained active and all were alive.

EXAMPLE XXIV

Petri dishes were prepared containing a thin layer of bean agar. A thin layer of hot paraffin wax was poured over the agar. When the wax cooled, its surface was broken by penetrating with a circle of points mounted on a hot iron. The dishes were sprayed with an aqueous dispersion of one of the hereinafter set forth compounds. The aqueous dispersion was prepared by dispersing a predetermined amount of one of the test compounds and a predetermined amount of a surfactant in a predetermined amount of water. At the same time additional dishes were sprayed with a water/surfactant mixture containing none of the compounds. The surface of the dishes were infested with codling moth egg and the dishes maintained under conditions conducive to the hatching of the eggs and growth of the larvae therefrom. Ten days after treatment, the dishes were examined for the presence of frass piles (excrement piles) the number of which were taken as an indication of the number and presence of active larvae. The results of this examination are set forth below in Table VIII.

TABLE VIII

| Number of active Compound | Concentration in PPM of active compound in aqueous dispersion | Percent Kill and control of codling moth larvae |
|---|---|---|
| 1 | 400 | 50 |
| 2 | 400 | 80 |
| 3 | 400 | 100 |
|   | 100 | 100 |
|   | 25 | 100 |
| 4 | 400 | 100 |
|   | 100 | 80 |
| 5 | 400 | 90 |
|   | 100 | 70 |
|   | 25 | 50 |
| 8 | 400 | 100 |
|   | 100 | 70 |
| 9 | 400 | 100 |
| 11 | 400 | 100 |
| 13 | 400 | 100 |
|   | 100 | 100 |
|   | 25 | 100 |
| 16 | 400 | 90 |
| 18 | 400 | 100 |
|   | 100 | 80 |
| 20 | 400 | 100 |
|   | 100 | 100 |
| 21 | 400 | 100 |
|   | 100 | 70 |
|   | 25 | 80 |
| 23 | 400 | 100 |
|   | 100 | 100 |
|   | 25 | 80 |
| 24 | 400 | 100 |
|   | 100 | 90 |
|   | 25 | 70 |
| 25 | 400 | 100 |
|   | 100 | 100 |
|   | 25 | 90 |
| 26 | 400 | 100 |
| 29 | 400 | 100 |
|   | 100 | 100 |
| 30 | 400 | 100 |
|   | 100 | 75 |
| 33 | 400 | 100 |
| 34 | 400 | 50 |
| 35 | 400 | 100 |
| 37 | 400 | 100 |
| 38 | 400 | 90 |
| 39 | 400 | 100 |
| 44 | 400 | 100 |
| 45 | 400 | 100 |
| 53 | 400 | 100 |
|   | 100 | 60 |
|   | 25 | 50 |
| 54 | 400 | 95 |
|   | 100 | 50 |
|   | 25 | 50 |
| 60 | 400 | 100 |
| 61 | 400 | 100 |
| 71 | 400 | 100 |
| ControL | — | 0 |

EXAMPLE XXV

Seventy-five grams of air-dried soil was placed in an 8-ounce container. To the soil was added sufficient volume of a 400 ppm aqueous dispersion, prepared by admixing a predetermined amount of one of the hereinafter set forth compounds with a predetermined amount of water and a predetermined amount of a surfactant, to give various predetermined concentrations of the toxicant in the soil on a soil-chemical basis. The treated soil was air-dried and thoroughly mixed by agitation. To each treated container, and control containers treated with water and surfactant alone, was added 0.5 milliliters of an aqueous suspension of the eggs of the Western spotted cucumber beetle (WSCB) (70–80 eggs of 3–4 days old). Additional treated soil was used to cover the eggs and cucumber seed was placed on the soil and covered with additional treated soil. The containers were thereafter maintained under conditions conducive to the growth of the seeds and the hatching of the eggs. Twelve (12) days after treatment, the containers and the plants therein were examined to determine the degree of the kill and control of the larvae from the hatched eggs. The results of this examination are set forth below in Table IX.

TABLE IX

| Number of active Compound | Concentration in PPM of active compound in soil | Percent Kill and Control of WSCB larvae |
|---|---|---|
| 2 | 25 | 100 |
|   | 6 | 100 |
|   | 1.5 | 100 |
| 3 | 25 | 100 |
| 4 | 25 | 100 |
| 5 | 25 | 100 |
|   | 6 | 100 |
|   | 1.5 | 100 |
| 8 | 25 | 100 |
|   | 6 | 100 |
| 9 | 25 | 100 |
|   | 6 | 100 |
| 13 | 25 | 100 |
|   | 6 | 100 |
|   | 1.5 | 100 |
| 15 | 25 | 100 |
|   | 6 | 100 |
|   | 1.5 | 100 |
| 16 | 25 | 100 |
|   | 6 | 50 |
| 19 | 25 | 100 |
| 20 | 25 | 100 |
| 21 | 25 | 100 |
|   | 6 | 100 |
|   | 1.5 | 100 |
| 23 | 25 | 100 |
|   | 6 | 100 |
|   | 1.5 | 100 |
| 24 | 25 | 100 |
|   | 6 | 100 |
| 25 | 25 | 100 |
|   | 6 | 100 |
| 30 | 25 | 100 |
|   | 6 | 100 |
| 37 | 25 | 100 |
| 38 | 25 | 100 |
| 39 | 25 | 100 |
|   | 6 | 50 |
| 42 | 25 | 100 |
| 43 | 25 | 100 |
| 44 | 25 | 100 |
| 45 | 25 | 50 |
| 53 | 25 | 100 |
| 66 | 25 | 100 |
| Control | — | 0 |

EXAMPLE XXVI

Each of the hereinafter set forth compounds were employed for the control of two-spotted spider mites. In this operation, the compounds were separately dispersed in a quantity of water to prepare an aqueous dispersion containing 400 parts of one of the test compounds as the sole active toxicant, per million parts by weight of ultimate dispersion. Stands of young cranberry bean plants, heavily infested with two-spotted spider mites, were thoroughly wetted with one of the test dispersions. Thereafter the wetted plants were permitted to dry and the dried plants held for a period of 6 days under conditions conducive to the continued growth of two-spotted spider mite populations. Untreated stands of young cranberry bean plants heavily infested with two-spotted spider mites were held for the same period of time under the same conditions to serve as controls. At the end of the period, all of the plants were examined and it was found that in the plants treated with the test compounds, there was obtained a 100 percent kill and control of two-spotted spider mites, while on the control plants, there was a heavy infestation of two-spotted spider mites.

The compounds employed as test compounds in this operation were compounds numbered 15, 16, 34 38, 39, 44, 52 and 55.

EXAMPLE XXVII

Each of the hereinafter set forth compounds were employed for the control of beet armyworm larvae. In this operation, each of the compounds was dispersed in a quantity of water to prepare an aqueous dispersion containing 400 parts of one of the compounds, as sole active toxicant, per million parts by weight of ultimate dispersion. Stands of young cranberry bean plants were thoroughly wetted briefly with the dispersion and the wetted plants permitted to dry. After the plants were dry, 5 live beet armyworm larvae were placed on each plant of the stand. In identical operations, 5 live beet armyworm larvae were placed on each plant in control stands of untreated young cranberry bean plants. Each of the stands was maintained for a period of about 6 days under conditions favorable to the growth of the larvae. At the end of the 6-day period, all of the plants were examined; in the treated stands, there was found a 100 percent kill and control of beet armyworms, while a thriving population of live beet armyworm larvae continued to feed on the plants of the control stands.

The compounds employed as test compounds in this operation were compounds numbered 18, 24, 25, 29, 43, 44 and 45.

In another operation, each of the compounds numbered 2-4, 6, 8, 9, 11, 13-16, 18, 29, 30, 32, 35, 39, 44, 45, 52, 54 and 55, were found to give 100 percent kill and control of brown dog tick when applied thereto in an aqueous dispersion containing one of the compounds as the sole toxicant, at 500 milligrams per 100 cubic centimeters of the ultimate dispersion.

In another operation, each of the compounds numbered 5, 9, 26, 34, 35, 52, 54, 56, 60, 61, 65, 66 and 71 were found to give at least 50 percent kill and control of the cabbage looper when applied to the habitat thereof in an aqueous dispersion, as the sole toxicant, at 400 parts of the compound per million parts of the ultimate dispersion.

In other operations, each of the compounds numbered 2, 5, 9, 13, 15, 16, 25, 29, 30, 39, 45 and 54 were found to give at least 50 percent kill and control of bollworms when applied thereto in an aqueous dispersion containing one of the compounds, as the sole toxicant, at 400 parts of the compound per million parts of the ultimate dispersion.

What is claimed is:

1. A compound corresponding to the formula

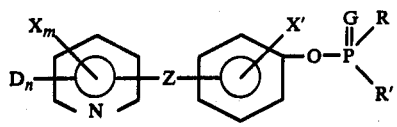

wherein each X independently represents chloro, fluoro or bromo; X' represents hydrogen, methyl, chloro, bromo or fluoro; G represents oxygen or sulfur; Z represents oxygen, sulfur, sulfinyl or sulfonyl, with the proviso that Z is attached to the pyridine ring in only the 2 or 4 ring position; D represents cyano in the alpha- or 6-position; R represents loweralkylthio, loweralkoxy, loweralkylamino of 1 to 4 carbon atoms or diloweralkylamino of 1 to 4 carbon atoms; R' represents R or phenyl; m represents an integer of from 0 to 4; n represents 1 and the sum of m + n represents an integer of from 0 to 4.

2. An insecticidal composition comprising as an active ingredient, an insecticidally effective amount of a compound corresponding to the formula

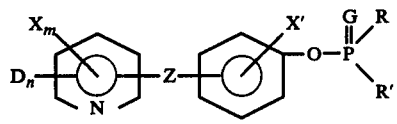

wherein each X independently represents chloro, fluoro or bromo; X' represents hydrogen, methyl, chloro, bromo or fluoro; G represents oxygen or sulfur; Z represents oxygen, sulfur, sulfinyl or sulfonyl, with the proviso that Z is attached to the pyridine ring in only the 2 or 4 ring position; D represents cyano in the alpha- or 6-position; R represents loweralkylthio, loweralkoxy, loweralkylamino of 1 to 4 carbon atoms or diloweralkylamino of 1 to 4 carbon atoms; R' represents R or phenyl; m represents an integer of from 0 to 4; n represents 1 and the sum of m + n represents an integer of from 0 to 4, in intimate admixture with an inert carrier therefor.

3. A method for the kill and control of insects which comprises contacting said insects or their habitat with a composition containing as the active ingredient an insecticidally effective amount of a compound corresponding to the formula

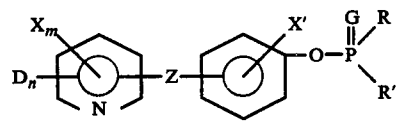

wherein each X independently represents chloro, fluoro or bromo; X' represents hydrogen, methyl, chloro, bromo or fluoro; G represents oxygen or sulfur; Z represents oxygen, sulfur, sulfinyl or sulfonyl, with the proviso that Z is attached to the pyridine ring in only the 2 or 4 ring position; D represents cyano in the alpha- or 6-position; R represents loweralkylthio, loweralkoxy, loweralkylamino of 1 to 4 carbon atoms or diloweralkylamino of 1 to 4 carbon atoms; R' represents R or phenyl; m represents an integer of from 0 to 4; n represents 1 and the sum of m + n represents an integer of from 0 to 4, in intimate admixture with an inert carrier therefor.

* * * * *

UNITED STATES PATENT AND TRADEMARK OFFICE
CERTIFICATE OF CORRECTION

PATENT NO. : 4,132,784

DATED : January 2, 1979

INVENTOR(S) : Sudarshan K. Malhotra

It is certified that error appears in the above-identified patent and that said Letters Patent are hereby corrected as shown below:

Column 4, line 8, "structureof" should read -- structure of --;

Column 4, line 63, "O-[6-(4-(((-diethoxyphosphinothionyl-" should read -- O-[6-(4-(((-diethoxyphosphinothioyl- --;

Column 5, "Formula" at top of TABLE I should read as follows:

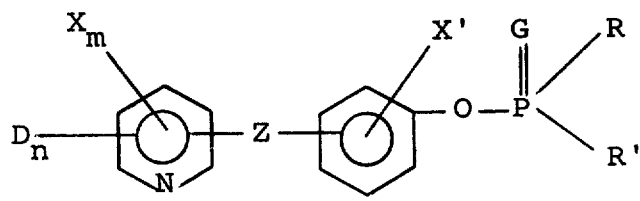

Column 6, Table I, Compound 18 under column heading "Physical[a] Properties" should read -- M.P. = 42° - 45°C --;

Column 6, Table I, Compound 70 under column heading "Physical[a] Properties" should read -- M.W. = 438.25 --;

Column 15, line 32 "dispensing" should read -- dispersing --;

Column 15, line 35 "concentrated" should read -- concentrates --;

Column 16, line 23 "product" should read -- products --;

Column 16, line 24 "back" should read -- pack --;

UNITED STATES PATENT AND TRADEMARK OFFICE
CERTIFICATE OF CORRECTION

PATENT NO. : 4,132,784
DATED : January 2, 1979
INVENTOR(S) : Sudarshan K. Malhotra It is certified that error appears in the above-identified patent and that said Letters Patent are hereby corrected as shown below:

Column 20, TABLE VI, Compound No. 2 under column heading "Percent mortality of cockroaches" should read -- 80 --.

Signed and Sealed this

First Day of May 1979

[SEAL]

Attest:

RUTH C. MASON
Attesting Officer

DONALD W. BANNER
Commissioner of Patents and Trademarks